United States Patent

Howes

(10) Patent No.: US 9,795,293 B2
(45) Date of Patent: Oct. 24, 2017

(54) UNIVERSAL ADAPTER FOR CAMERA-CONTAINING HANDHELD DEVICE

(71) Applicant: Transamerican Technologies International, San Ramon, CA (US)

(72) Inventor: Allen R. Howes, Danville, CA (US)

(73) Assignee: Transamerican Technologies International, San Ramon, CA (US)

(*) Notice: Subject to any disclaimer, the term of this patent is extended or adjusted under 35 U.S.C. 154(b) by 142 days.

(21) Appl. No.: 14/829,544

(22) Filed: Aug. 18, 2015

(65) Prior Publication Data

US 2016/0051142 A1 Feb. 25, 2016

Related U.S. Application Data

(60) Provisional application No. 62/040,922, filed on Aug. 22, 2014.

(51) Int. Cl.
| | | |
|---|---|---|
| *A61B 3/14* | (2006.01) | |
| *A61B 3/135* | (2006.01) | |
| *G03B 17/56* | (2006.01) | |
| *A61B 3/10* | (2006.01) | |

(52) U.S. Cl.
CPC .............. *A61B 3/14* (2013.01); *A61B 3/10* (2013.01); *G03B 17/561* (2013.01); *G03B 17/565* (2013.01)

(58) Field of Classification Search
CPC .......... A61B 3/14; A61B 3/10; G03B 17/561; G03B 17/17565
USPC ......................................................... 396/420
See application file for complete search history.

(56) References Cited

U.S. PATENT DOCUMENTS

| | | | |
|---|---|---|---|
| 4,504,129 | A | 3/1985 | Van Iderstine |
| 4,767,204 | A | 8/1988 | Blaha |
| 5,264,928 | A | 11/1993 | Howes |
| 5,787,701 | A | 8/1998 | Small |
| 5,934,061 | A | 8/1999 | Smith |

(Continued)

FOREIGN PATENT DOCUMENTS

CN 202841224 U 3/2013

OTHER PUBLICATIONS

ACCU-Beam, "iPhone Adaptor for Haag Streit 900BM Style Slit Lamps," TTI Medical Product Details, Jan. 9, 2013, San Ramon CA, 1 pg.

(Continued)

*Primary Examiner* — Rochelle-Ann J Blackman
(74) *Attorney, Agent, or Firm* — James F. Hann; Haynes Beffel & Wolfeld LLP (57) ABSTRACT

A device adapter is used to mount a handheld device, such as a smartphone, to the binocular tube of a microscope, such as a slit lamp. The handheld device has a camera, a device surface on one side, and a camera lens at the one side. The adapter includes a body with an abutment surface, two side grippers and a lower gripper used to secure the device against the abutment surface of the body. The device adapter also includes an adapter assembly including a camera lens opening alignable with a handheld device camera lens so that an image entering the outer end of the ocular tube with integrated optics passes through the ocular tube, through the integrated optic, and through the camera lens opening for passage into the camera lens.

15 Claims, 7 Drawing Sheets

(56) References Cited

U.S. PATENT DOCUMENTS

| | | | |
|---|---|---|---|
| 6,113,533 | A | 9/2000 | Howes et al. |
| 6,155,973 | A | 12/2000 | Howes et al. |
| 7,465,049 | B2 | 12/2008 | Maeda et al. |
| 8,746,885 | B2 | 6/2014 | Raskar et al. |
| 9,131,132 | B2 | 9/2015 | Graether |
| 2012/0287402 | A1 | 11/2012 | Davis |
| 2014/0072362 | A1 | 3/2014 | Hyers |
| 2015/0042873 | A1* | 2/2015 | Hunt .................. H04N 5/2254 348/373 |
| 2015/0070580 | A1 | 3/2015 | Graether |

OTHER PUBLICATIONS

ACCU-Beam, "Digital Eyepiece Camera Kit for Haag Streit 900BM Style Lit Lamps for Canon ELPH 300 or IXUS 220," TTI Medical Product Details, Aug. 1, 2011, San Ramon CA, 2 pgs.
ACCU-Beam, "Digital Eyepiece Camera Kit for Haag Streit 900BM Style Lit Lamps for Canon A2600," TTI Medical Product Details, Jul. 10, 2013, San Ramon CA, 2 pgs.

* cited by examiner

UNIVERSAL ADAPTER FOR CAMERA-CONTAINING HANDHELD DEVICE

CROSS-REFERENCE TO OTHER APPLICATIONS

This application claims the benefit of U.S. provisional patent application No. 62/040,922, filed 22 Aug. 2014, the disclosure of which is incorporated by reference.

BACKGROUND OF THE INVENTION

Slit lamps are often used by ophthalmologists to examine the patient's eye. Often photographic documentation is needed to assist in the diagnosis of the eye disorder. The optical quality of pictures taken by smart phones and the flexibility associated with the use of smart phones have created a robust market for use of smart phone adapters to capture images from microscopes, such as the slit lamp type of microscope. The present invention is universally adaptable to a wide range of microscopes and hand held devices with a camera, such as smart phones, available now and in the future.

BRIEF SUMMARY OF THE INVENTION

A device adapter made according to the present invention is a simple, easy-to-use, inexpensive device to permit a smart phone, or other handheld devices having a camera, to capture images from a microscope, such as a slip lamp. The device adapter can be used with a wide range of different microscopes having different diameter binocular tubes through the use of simple adapter sleeves. The device adapter can be used with both converging optic slit lamps and parallel optic slit lamps.

A device adapter is used to mount a handheld device, such as a smartphone, to the binocular tube of a microscope, the handheld device having a camera, a device surface and a camera lens opening positioned along the device surface. The adapter includes a body, first and second side grippers, a lower gripper, and an adapter assembly. The body has a periphery defined by first and second sides, an upper end and a lower end. The body also has an abutment surface extending between the first and second sides. The first side gripper is supported by the body at the first side and has a first gripping element positioned outwardly of the abutment surface. The second side gripper is supported by the body at the second side and has a second gripping element positioned outwardly of the abutment surface. The second side gripper is an adjustable position gripper movable towards and away from the first gripper along a line parallel to an X axis so the distance between the first and second gripping elements can be changed to accommodate different size devices. A side gripper locking assembly secures the second side gripper to the body at first chosen positions along a first line parallel to the X axis. The lower gripper is supported by the body at the lower end and has a lower gripping element positioned outwardly of the abutment surface. The lower gripper is an adjustable position gripper movable along a line parallel to a Y axis so the distance between the lower gripping element and the upper end of the body can be changed to accommodate different size devices. The X and Y axes are transverse to one another. A lower gripper locking assembly secures the lower gripper to the body at second chosen positions along a second line parallel to the Y axis. The adapter assembly is mounted to and extends upwardly above the upper end of the body for movement parallel to the X axis. The adapter assembly includes an adapter assembly body with a camera lens opening generally aligned with the abutment surface of the body, and an ocular tube with integrated optics having an outer end extending from the adapter assembly body. An adapter assembly positioner couples the adapter assembly body and the body to position the adapter assembly along a third line parallel to the X axis. The camera lens opening is alignable with a handheld device camera lens based upon at least the second and third chosen positions so that an image entering the outer end of the ocular tube with integrated optics passes through the ocular tube, through the integrated optic, and through the camera lens opening for passage into the camera lens.

Examples of the device adapter can include one or more the following. The abutment surface can comprise a releasable, reusable adhesive surface to help secure the handheld device to the adapter. The second side gripper can include a slotted arm, having an outer end and an elongate slotted recess, and a gripping element support mounted to the outer end of the slotted arm, the second gripping element mounted to the gripping element support, with the side gripper locking assembly including a sliding nut slidably positioned within the slotted recess, and a position locking screw passing through the body and engaging the sliding nut. The adapter assembly body can include an adapter body extension with a threaded bore, and the adapter assembly positioner can include a lead screw supported by the body and threadably engaging the threaded bore so that rotating the lead screw causes the adapter body to move along the third line. An adapter assembly locking assembly can be used to secure the adapter assembly body to the body at third chosen positions along the third line, the adapter assembly locking assembly including a locking screw passing through the body and threadably engaging the adapter body extension. The adapter assembly can include a telescoping ring, a rotatable focusing ring, and a guide element, with the telescoping ring movably mounted to the adapter assembly body for movement along a Z axis, the telescoping ring having a first set of threads, the rotatable focusing ring rotatably mounted to the adapter assembly body and having a second set of threads complementary to and engaging the first set of threads, and the guide element coupling the telescoping ring and the adapter assembly body to permit movement of the telescoping ring along the Z axis while preventing relative rotary motion between the telescoping ring and the adapter assembly body; the ocular tube with integrated optics can be mounted to the telescoping ring for movement along the z-axis. The X, Y and Z axes can be perpendicular to one another. A set of hollow adapter sleeves can be used to mount over the ocular tube to permit the adapter to be used with binocular tubes having larger inside diameters.

Other features, aspects and advantages of the present invention can be seen on review of the drawings, the detailed description, and the claims which follow.

DETAILED DESCRIPTION

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Unless otherwise stated, in this application specified relationships, such as parallel to, aligned with, or in the same plane as, mean that the specified relationships are within limitations of manufacturing processes and within manufacturing variations. When components are described as being coupled, connected, being in contact or contacting one another, they need not be physically directly touching one another unless specifically described as such. Like elements in various embodiments are commonly referred to with like reference numerals.

Figure 1:
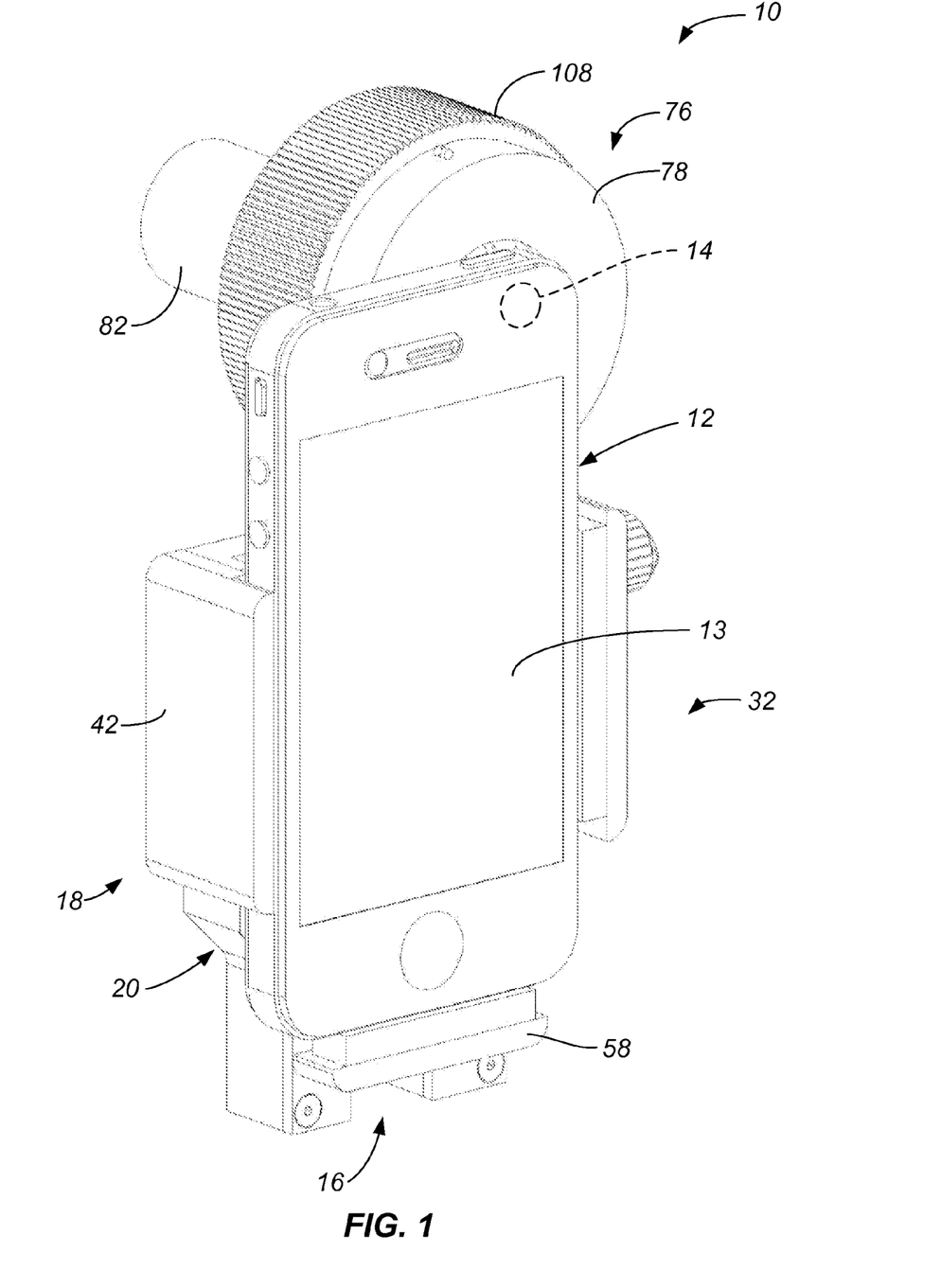
FIG. 1 is an overall view of a device adapter to which a smart phone type of handheld device with a camera has been mounted.

FIG. 1 illustrates the device adapter 10 to which the smart phone 12 having a camera with a camera lens 14 positioned, in this example, on the opposite side of smart phone 12. Instead of smart phone 12, other types of handheld devices having a camera can also be used with device adapter 10. Smart phone 12 has a screen 13 to permit the user to view the image in real time and, if desired, capture and save the image according to the abilities of smart phone.

Figure 2:
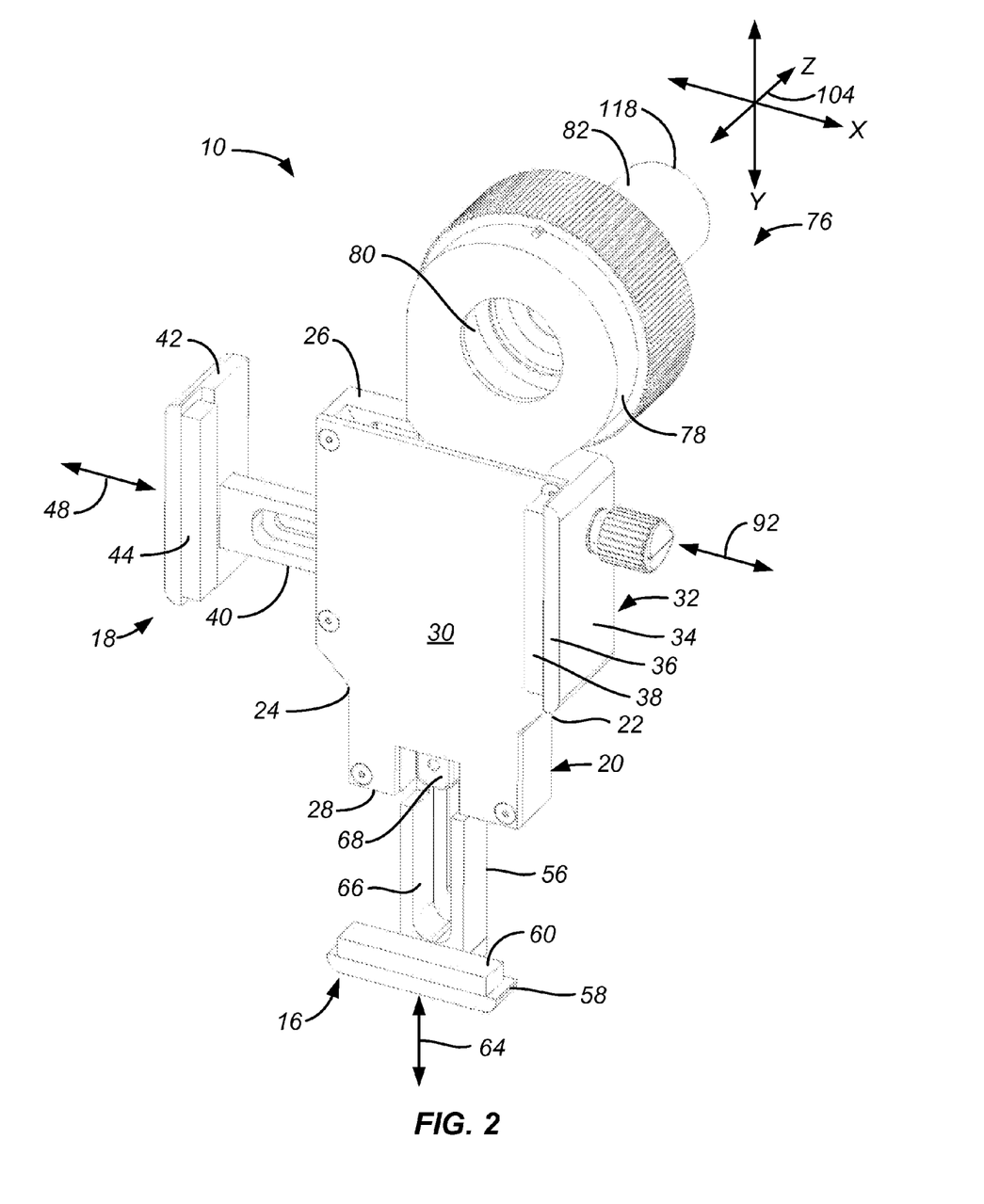
FIG. 2 shows the device adapter of FIG. 1 with the handheld device removed and a lower gripper and a side gripper at extended positions relative to the body of the device adapter.

FIG. 2 shows the device adapter 10 of FIG. 1 with the smart phone 12 removed and a lower gripper 16 and a left side gripper 18 at extended positions relative to the body 20 of the device adapter. Body 20 has a periphery defined by a first or right side 22, a second or left side 24, an upper end 26 and a lower end 28. An abutment surface 30 extends between right and left sides 22, 24. Surface 30 is designed to abut a surface of smart phone 12. To help retain smart phone 12 in place, surface 30 is preferably a releasable, reusable adhesive surface. One way to provide an adhesive abutment surface 30 is to mount a cushioned pad to surface 30, typically using a permanent adhesive on the surface of the pad contacting surface 30. The pad can be of a commercially available type, often made of polyurethane, having a surface which can be washed and reused. US patent publication 2015/0070580 A1, inventor Graether, discloses the use of a reusable adhesive pad on a camera phone mount. In some examples other types of double-sided adhesive structures, including those with releasable adhesives, which may or may not be reusable, on both sides, can be used.

Device adapter 10 also includes a right side gripper 32 which, in this example, is not adjustable. Right side gripper 32 includes a right side gripper element support 34 extending from right side 22 of body 20 with a portion 36 extending outwardly of abutment surface 30. A first or right gripping element 38 is mounted to portion 36 and also extends outwardly of abutment surface 30. In other examples right side gripper 32 could be an adjustable position gripper.

Figure 3:
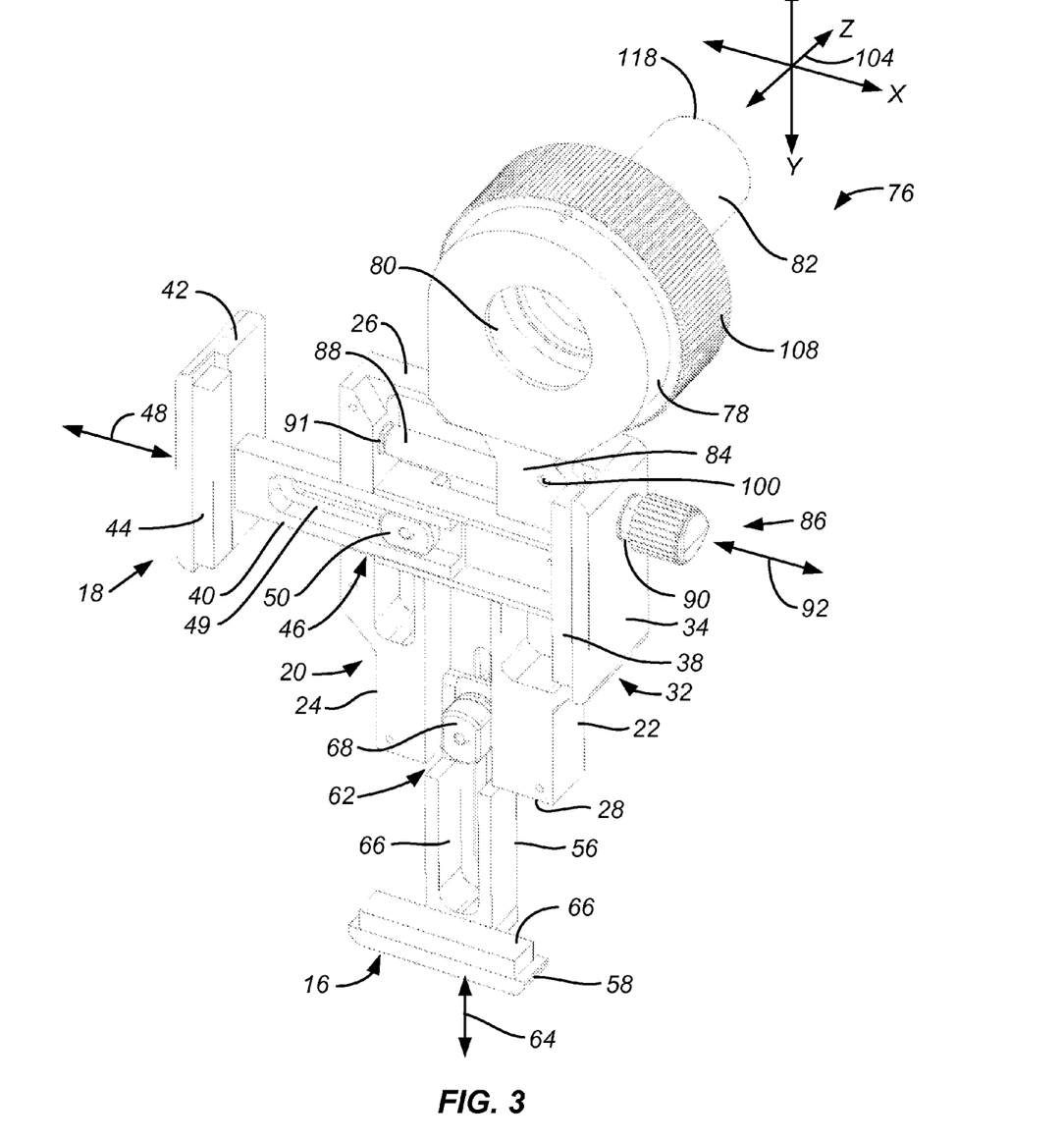
FIG. 3 shows the device adapter of FIG. 2 with the portion of the body including the abutment surface removed to show the inner workings of several components of the device adapter.
Figure 4:
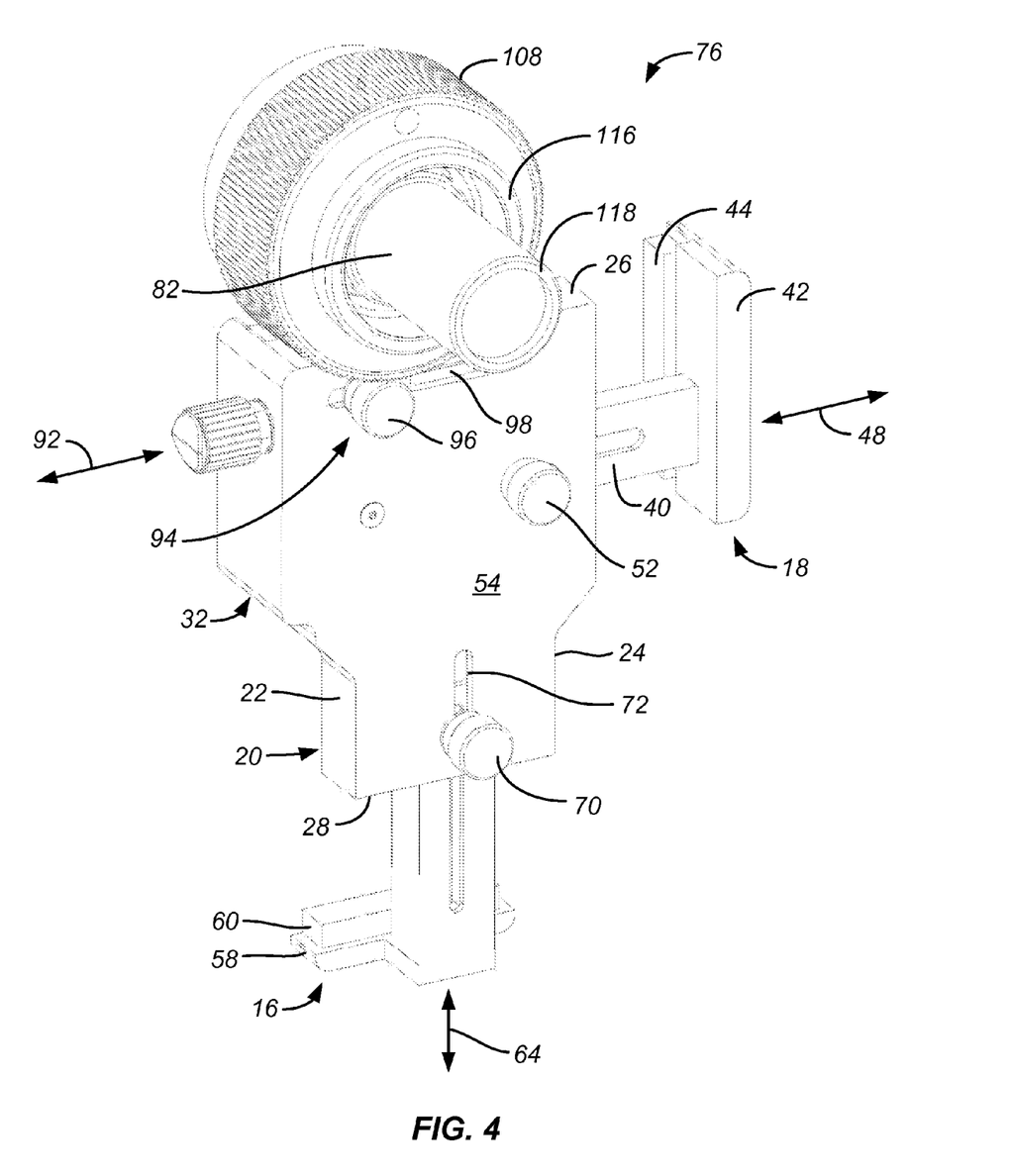
FIG. 4 shows the device adapter of FIG. 2 from the opposite side.

Left side gripper 18 includes a slotted arm 40 with a left side gripper element support 42 extending from its outer end. A second or left gripping element 44 is mounted to left side gripper element support 42. Left gripping element 44 is positioned opposite right gripping element 38 and outwardly of abutment surface 30. FIG. 3 illustrates a side gripper locking assembly 46 used to secure the left side gripper 18 at chosen positions along a line 48 parallel to an X axis. Slotted arm 40 has an elongate slotted recess 49 along its length housing a sliding nut 50. Sliding nut 50 is connected to a position locking screw 52, see FIG. 4, passing through an opening in the back surface 54 of body 20. In some examples side gripper locking assembly 46 can be a spring type locking assembly by which a spring biases left gripping element 44 against the edge of smart phone 12, preferably with a user-adjustable force. Also, clips or other types of retainers can be mounted to one or more of right side gripper element support 34, left side gripper element support 42 and lower gripper element support 58 to be positionable opposite the screen-side of smart phone 12 to help secure smart phone 12 to device adapter 10. In addition, the shape of gripping elements 38, 44 and 60 can be made to conform to the shape of the edge surfaces of smart phone 12, Lower gripper 16, see FIG. 2, includes a slotted arm 56 with a lower gripper element support 58 extending from its outer end. A lower gripping element 60 is mounted to lower gripping element support 58 and is positioned outwardly of abutment surface 30. FIG. 3 illustrates a lower gripper locking assembly 62 used to secure the lower gripper 16 at chosen positions along a line 64 parallel to a Y axis. Slotted arm 56 has an elongate slotted recess 66 along its length housing a sliding nut 68. Sliding nut 68 is connected to a position locking screw 70, see FIG. 4, passing through an opening 72 in the back surface 54 of body 20. Smart phone 12 can be secured to device adapter 10 by the engagement of gripping elements 38, 44, and 60 as well as the adhesion provided by abutment surface 30 when it is an adhesive surface. Gripping elements 38, 44 and 60 are, in this embodiment, made of polyurethane cushion material to securely grip the edges of smart phone 12 while not damaging the smart phone. In some examples the surfaces of one or more of the gripping elements 38, 44 and 60 engaging smart phone 12 can be washable, reusable adhesive surfaces.

An adapter assembly 76 is mounted to and extends upwardly above the upper end 26 of body 20 for movement parallel to the X axis. Adapter assembly 76 includes an adapter assembly body 78, with a camera lens opening 80 generally aligned with abutment surface 30 of the body, and an ocular tube 82, having an outer end extending from the adapter assembly body 78. Adapter assembly body 78 has an adapter body extension 84 with a threaded bore, not shown but extending parallel to the X axis. An adapter assembly positioner 86 includes a lead screw 88 supported by body 20 at positions 90, 91. Lead screw 88 threadably engages the threaded bore in adapter body extension 84 so that rotating the lead screw causes the adapter assembly body 78 to move along a line 92 parallel to the X axis. An adapter assembly locking assembly 94, see FIG. 4, can be used to secure the adapter assembly body 78 to the body 20 at chosen positions along line 92. The adapter assembly locking assembly 94 includes a locking screw 96 threadably engaging a threaded hole 100 in the adapter body extension 84. Locking screw 96 passes through a slot 98 formed in back surface 54 of body 20 to permit a user to prevent adapter assembly 76 from moving along line 92. In some examples lead screw 88 could be configured to incorporate a locking feature preventing the lead screw from inadvertently rotating thus eliminating the need for the separate adapter assembly locking assembly 94.

Figure 5:
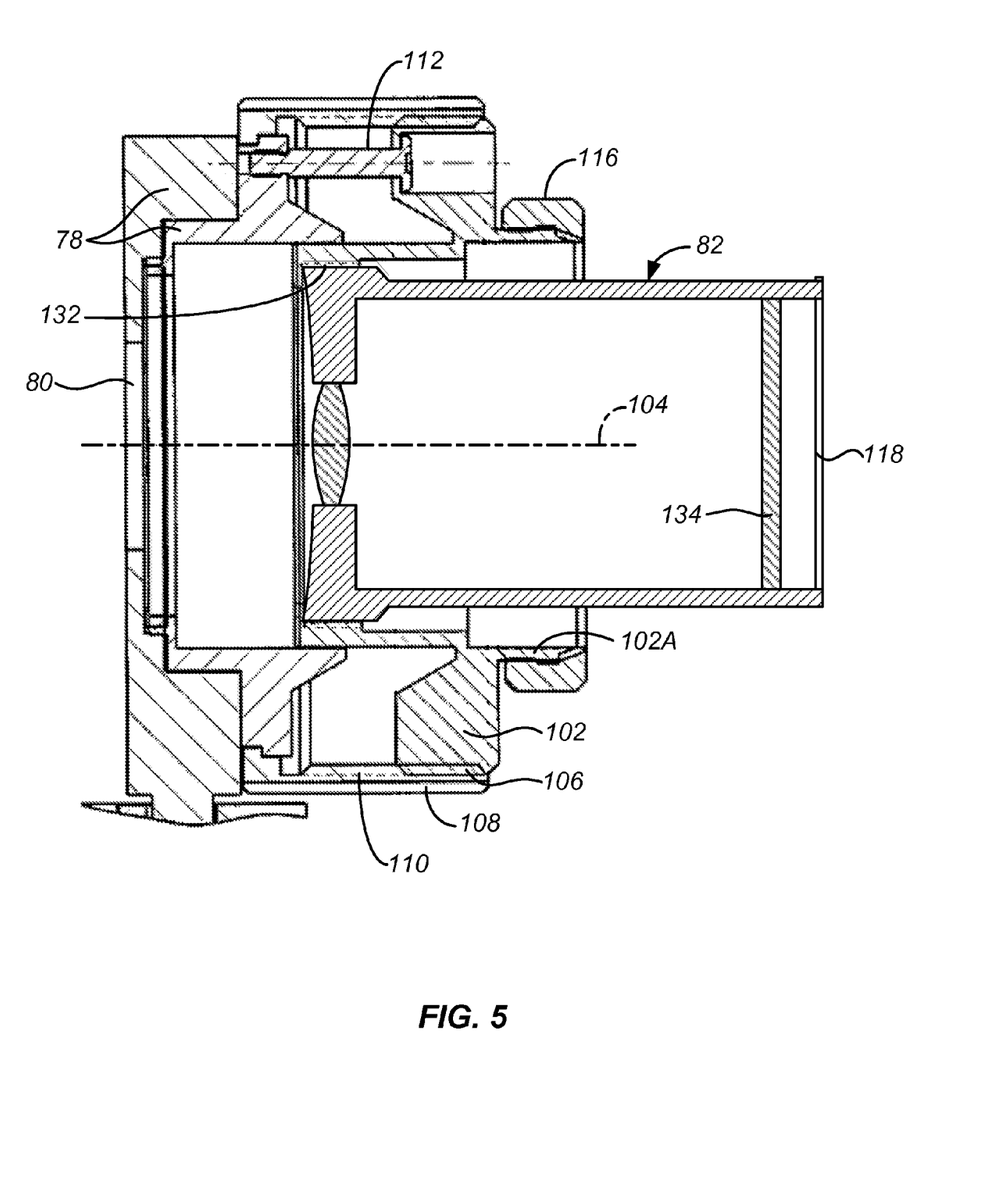
FIG. 5 is an enlarged cross-sectional view of a portion of the adapter assembly of FIGS. 1-4 showing an axially movable telescoping ring used to support the integrated optics of the adapter assembly at different positions along a Z axis.

Referring now also to FIG. 5, the adapter assembly 76 is shown to also include the ocular tube 82 with integrated optics, a telescoping ring 102 movably mounted to the adapter assembly body 78 for movement along a Z axis 104. In FIG. 5 ocular tube 82 with integrated optics is secured to telescoping ring 102 at location 132 and has a transparent window 134 near its outer end 118. The telescoping ring 102 has external threads 106 extending around its periphery. Adapter assembly 76 also includes a rotatable focusing ring 108 rotatably mounted to the adapter assembly body 78. Ring 108 has internal threads 110 complementary to and engaging external threads 106. A guide element 112 couples the telescoping ring 102 and the adapter assembly body 78 to permit movement of the telescoping ring along the Z axis 104 while preventing relative rotary motion between the telescoping ring and the adapter assembly body. Therefore, when focusing ring 108 is rotated, telescoping ring 102 cannot rotate with the focusing ring and therefore, due to the threaded engagement between the two pieces, telescoping ring 102 moves axially along the Z axis 104. This causes the position of optical tube 82 with integrated optics to move along the Z axis 104 to provide the proper focus for the camera through the camera lens 14 of smart phone 12. Adapter assembly 76 also includes a locking ring 116. During use the eyepiece of a microscope, one example of a microscope being a slit lamp, is removed from the binocular tube of the microscope and ocular tube 82 is inserted into the binocular tube. Locking ring 116 is used to secure the device adapter 10 to the binocular tube of the microscope by screwing locking ring 116 clockwise towards telescoping ring 102 causing the threaded extension 102A of telescoping ring 102 to clamp onto the eyepiece port of the binocular tube. In this application the term binocular tube is used whether or not the microscope has two binocular tubes or other than two binocular tubes.

Figure 6:
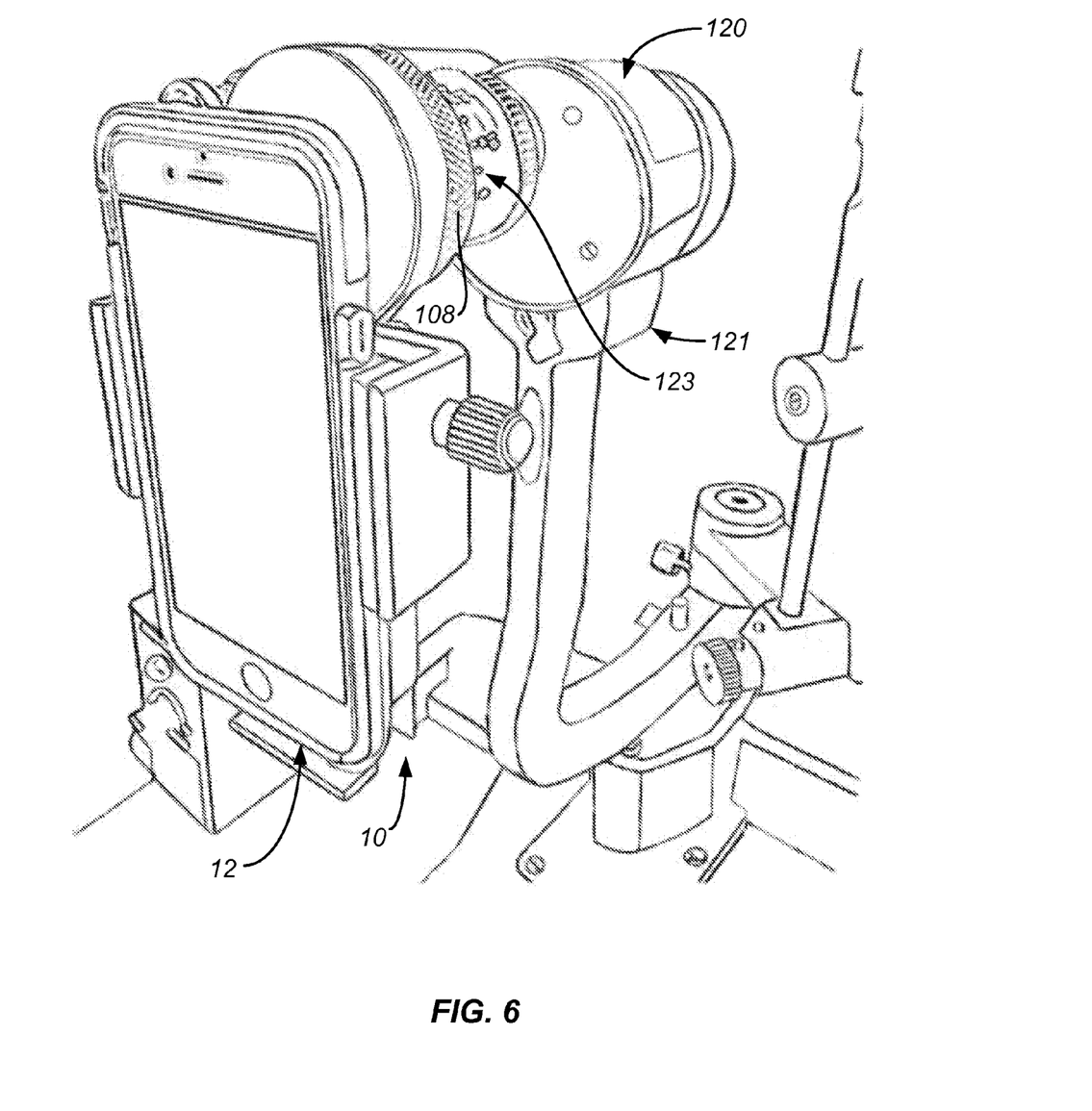
FIG. 6 is an overall view showing the device adapter and handheld device of FIG. 1 mounted to a binocular tube of a microscope.

During use, lower gripper 16 is positioned along line 64 so that the camera lens of the smart phone 12 is at the same height as camera lens opening 80. Smart phone 12 is then positioned to rest against right gripping element 38, lower gripping element 60 and against abutment surface 30. Abutment surface 30 is preferably a cleanable adhesive surface to help ensure that smart phone 12 does not become dislodged from device adapter 10. Left side gripper 18 is then moved along line 48 so that left gripping element 44 engages the left edge of smart phone 12 as shown in FIG. 1. The horizontal, that is x-axis, alignment of camera lens opening 80 with the camera lens 14 is achieved using adapter assembly positioner 86. Once properly positioned, the horizontal position of camera lens opening 80 secured in place using adapter assembly locking assembly 94. After removing an eyepiece (not shown in the figures) from a binocular tube 120 of a microscope 121, ocular tube 82 is inserted into the eyepiece port 123 at the outer end of the binocular tube and clamped in place using locking ring 116. FIG. 6 shows the device adapter 10 and smart phone 12 of FIG. 1 mounted to a binocular tube 120 of a slit lamp type of microscope 121. An image from the microscope 121 can then enter the outer end 118 of the ocular tube 82, pass through the ocular tube 82 containing integrated optics, and through the camera lens opening 80 for passage into the smart phone 12 through its camera lens 14. Proper focus is then achieved using focusing ring 108; rotating focusing ring 108 causes the position of ocular tube 82 with integrated optics, which effectively replaces the removed eyepiece, to move along Z axis 104. Images can then be displayed or saved, or both, using smart phone 12.

Figure 7A:
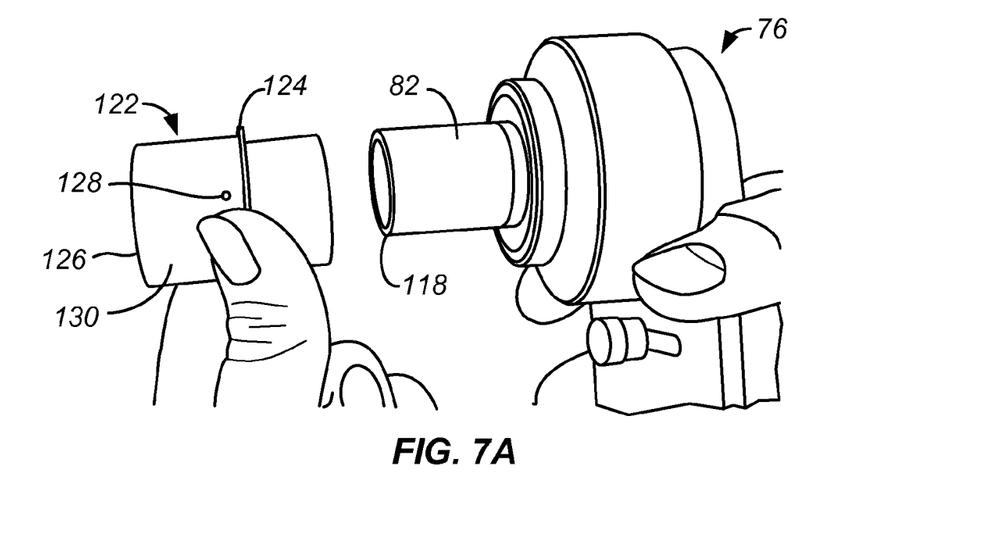
FIG. 7A shows a user about to place an adapter sleeve over the ocular tube of the adapter assembly so that the device adapter can be used with binocular tubes having a larger inside diameter than the outside diameter of the ocular tube of the adapter assembly.
Figure 7B:
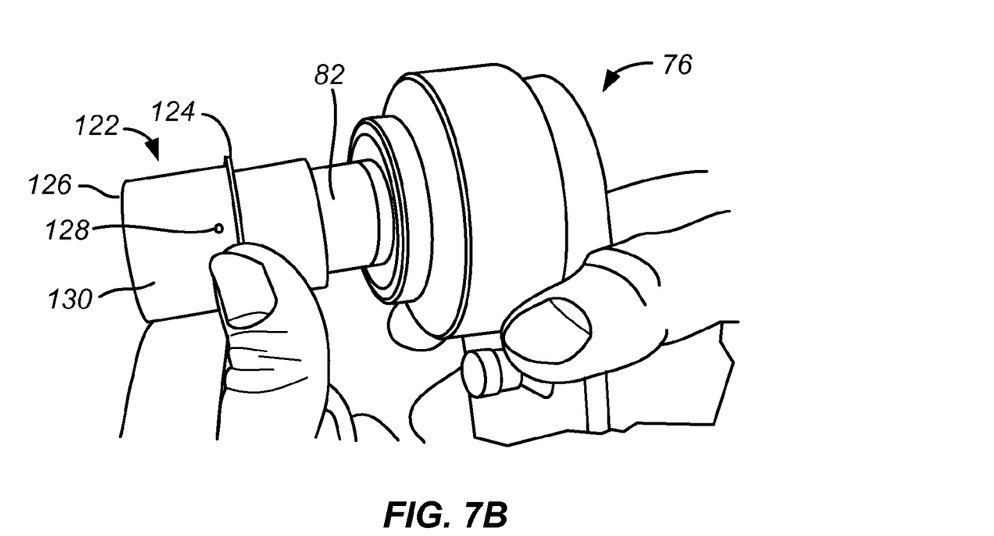
FIG. 7B shows the adapter sleeve partially mounted over the ocular tube.
Figure 8A:
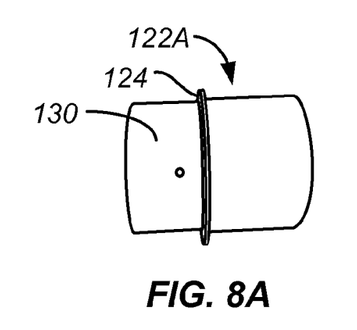
FIG. 8A and FIG. 8B show different sizes of adapter sleeves used for use with binocular tubes of different inside diameters.
Figure 8B:
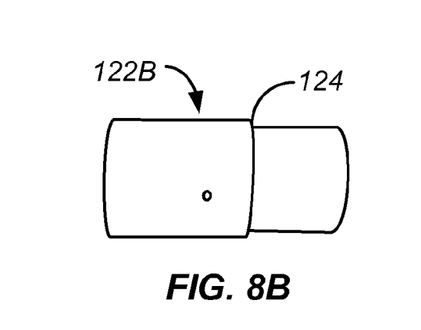

The binocular tubes of conventional microscopes have different size inside diameters. In this example ocular tube 82 has an outside diameter size to fit within the inside diameter of 23.5 mm binocular tubes. To accommodate the use of device adapter 10 with the fixed binocular tubes having larger inside diameters, an adapter sleeve 122 can be used. FIGS. 7A and 7B show the placement of adapter sleeve 122 over ocular tube 82 of adapter assembly 76. Adapter sleeve 122 has a shoulder 124 at position to engage a surface on the adapter assembly 76 so that the outer end 118 of ocular tube 82 is generally aligned with the outer end 126 of adapter sleeve 122. The axial length of the outer portion 130 of adapter sleeve 122 can be selected depending on the particular microscope, or group of microscopes, with which it is to be used. Adapter sleeve 122 is secured in place using a set screw 128. The outer end 126 of adapter sleeve 122 can then be placed within a larger-diameter binocular tube. In some examples a set of adapter sleeves 122, see FIGS. 8A and 8B, can be provided with the device adapter 10, or separately, to accommodate its use with a range of sizes of binocular tubes.

The above descriptions may have used terms such as above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims.

One or more elements of one or more claims can be combined with elements of other claims.

Any and all patents, patent applications and printed publications referred to above are incorporated by reference.

What is claimed is:

1. A universal device adapter for mounting a wide variety of handheld devices with digital cameras to the binocular tube of a microscope, such as the ophthalmic slit lamp, the handheld device having a camera, the adapter comprising:
  a body having a periphery defined by first and second sides, an upper end and a lower end, the body further comprising an abutment surface extending between the first and second sides;
  a first side gripper supported by the body at the first side and having a first gripping element positioned outwardly of the abutment surface;

a second side gripper supported by the body at the second side and having a second gripping element positioned outwardly of the abutment surface;

the second side gripper being an adjustable position gripper movable towards and away from the first gripper along a line parallel to an X axis so the distance between the first and second gripping elements can be changed to accommodate different size devices;

a side gripper locking assembly securing the second side gripper to the body at first chosen positions along a first line parallel to the X axis;

a lower gripper supported by the body at the lower end and having a lower gripping element positioned outwardly of the abutment surface;

the lower gripper being an adjustable position gripper movable along a second line parallel to a Y axis so the distance between the lower gripping element and the upper end of the body can be changed to accommodate different size devices, the X and Y axes being transverse to one another;

a lower gripper locking assembly securing the lower gripper to the body at second chosen positions along the second line parallel to the Y axis;

an adapter assembly mounted to and extending upwardly above the upper end of the body for movement parallel to the X axis;

the adapter assembly comprising an adapter assembly body with a camera lens opening generally aligned with the abutment surface of the body, and an ocular tube with integrated optics having an outer end extending from the adapter assembly body;

an adapter assembly positioner coupling the adapter assembly body and the body to position the adapter assembly along a third line parallel to the X axis;

the camera lens opening being alignable with a handheld device camera lens based upon at least the second and third chosen positions so that an image entering the outer end of the ocular tube with integrated optics passes through the ocular tube, through the integrated optic, and through the camera lens opening for passage into the camera lens.

2. The adapter according to claim 1, wherein said abutment surface comprises a releasable, reusable adhesive surface to help secure the handheld device to the adapter.

3. The adapter according to claim 1, wherein:

the second side gripper comprises a slotted arm, having an outer end and an elongate slotted recess, and a gripping element support mounted to the outer end of the slotted arm, the second gripping element mounted to the gripping element support;

the side gripper locking assembly comprises a sliding nut slidably positioned within the slotted recess, and a position locking screw passing through the body and engaging the sliding nut.

4. The adapter according to claim 1, wherein:

the adapter assembly body comprises an adapter body extension with a threaded bore; and the adapter assembly positioner comprises a lead screw supported by the body and threadably engaging the threaded bore so that rotating the lead screw causes the adapter body to move along the third line.

5. The adapter according to claim 4, further comprising an adapter assembly locking assembly securing the adapter assembly body to the body at third chosen positions along the third line, the adapter assembly locking assembly comprising a locking screw passing through the body and threadably engaging the adapter body extension.

6. The adapter according to claim 1, wherein the X and Y axes are perpendicular to one another.

7. The adapter according to claim 1, wherein:

the first gripping element is an elongate element and extends parallel to the Y axis;

the second gripping element is an elongate element and extends parallel to the Y axis; and the lower gripping element is an elongate element and extends parallel to the X axis.

8. The adapter according to claim 1, wherein both the first and second side grippers are adjustable position grippers.

9. The adapter according to claim 1, wherein the adapter assembly further comprises:

a telescoping ring movably mounted to the adapter assembly body for movement along a Z axis, the telescoping ring having a first set of threads;

a rotatable focusing ring rotatably mounted to the adapter assembly body and having a second set of threads complementary to and engaging the first set of threads; and a guide element coupling the telescoping ring and the adapter assembly body to permit movement of the telescoping ring along the Z axis while preventing relative rotary motion between the telescoping ring and the adapter assembly body; and wherein:

the ocular tube with integrated optics is mounted to the telescoping ring for movement along the z-axis.

10. The adapter according to claim 9, wherein the adapter assembly further comprises a locking ring rotatably mounted to the telescoping ring for use in securing the device adapter to the binocular tube of the microscope by rotating locking ring onto telescoping ring causing the telescoping ring to clamp onto the binocular tube.

11. The adapter according to claim 9, wherein the X, Y and Z axes are perpendicular to one another.

12. The adapter according to claim 1, wherein the ocular tube with integrated optics and the camera lens opening are aligned along a Z axis, the X, Y and Z axes being perpendicular to one another.

13. The adapter according to claim 1, further comprising a set of hollow adapter sleeves mountable over the ocular tube to permit the adapter to be used with binocular tubes having larger inside diameters.

14. A device adapter for mounting a handheld device to the binocular tube of a microscope, the handheld device having a camera, a device surface and a camera lens positioned along the device surface, the adapter comprising:

a body having a periphery defined by first and second sides, an upper end and a lower end, the body further comprising an abutment surface extending between the first and second sides;

said abutment surface comprising a releasable, reusable adhesive surface to help secure the handheld device to the adapter;

a first side gripper supported by the body at the first side and having a first gripping element positioned outwardly of the abutment surface;

a second side gripper supported by the body at the second side and having a second gripping element positioned outwardly of the abutment surface;

the second side gripper being an adjustable position gripper movable towards and away from the first gripper along a line parallel to an X axis so the distance between the first and second gripping elements can be changed to accommodate different size devices;

the second side gripper comprises a slotted arm, having an outer end and an elongate slotted recess, and a gripping element support mounted to the outer end of the slotted arm, the second gripping element mounted to the gripping element support;

a side gripper locking assembly securing the second side gripper to the body at first chosen positions along a first line parallel to the X axis;

the side gripper locking assembly comprises a sliding nut slidably positioned within the slotted recess, and a position locking screw passing through the body and engaging the sliding nut;

a lower gripper supported by the body at the lower end and having a lower gripping element positioned outwardly of the abutment surface;

the lower gripper being an adjustable position gripper movable along a second line parallel to a Y axis so the distance between the lower gripping element and the upper end of the body can be changed to accommodate different size devices;

a lower gripper locking assembly securing the lower gripper to the body at second chosen positions along the second line parallel to the Y axis;

an adapter assembly mounted to and extending upwardly above the upper end of the body for movement parallel to the X axis;

the adapter assembly comprising an adapter assembly body with a camera lens opening generally aligned with the abutment surface of the body, and an ocular tube with integrated optics having an outer end extending from the adapter assembly body;

an adapter assembly positioner coupling the adapter assembly body and the body to position the adapter assembly along a third line parallel to the X axis;

the adapter assembly body comprising an adapter body extension with a threaded bore;

the adapter assembly positioner comprising a lead screw supported by the body and threadably engaging the threaded bore so that rotating the lead screw causes the adapter body to move along the third line;

the camera lens opening being alignable with a handheld device camera lens based upon at least the second and third chosen positions so that an image entering the outer end of the ocular tube passes through the ocular tube, through the integrated optic, and through the camera lens opening for passage into the camera lens;

the adapter assembly further comprising:

a telescoping ring movably mounted to the adapter assembly body for movement along a Z axis, the telescoping ring having a first set of threads;

a rotatable focusing ring rotatably mounted to the adapter assembly body and having a second set of threads complementary to and engaging the first set of threads;

a guide element coupling the telescoping ring and the adapter assembly body to permit movement of the telescoping ring along the Z axis while preventing relative rotary motion between the telescoping ring and the adapter assembly body;

the ocular tube with integrated optics mounted to the telescoping ring for movement along the Z axis;

the ocular tube with integrated optics and the camera lens opening aligned along the Z axis, the X, Y and Z axes being perpendicular to one another; and a locking ring rotatably mounted to the telescoping ring for use in securing the device adapter to the binocular tube of the microscope by rotating locking ring onto the telescoping ring causing the telescoping ring to clamp onto the binocular tube.

15. The adapter according to claim 14, further comprising an adapter assembly locking assembly securing the adapter assembly body to the body at third chosen positions along the third line, the adapter assembly locking assembly comprising a locking screw passing through the body and threadably engaging the adapter body extension.

* * * * *